US008022033B2

(12) United States Patent
Larew et al.

(10) Patent No.: US 8,022,033 B2
(45) Date of Patent: Sep. 20, 2011

(54) ECHINOCANDIN/CARBOHYDRATE COMPLEXES

(75) Inventors: Larry Arnold Larew, Zionsville, IN (US); Nathaniel Milton, Indianapolis, IN (US); James Lawrence Sabatowski, Holland, MI (US); Kenneth Philip Moder, West Lafayette, IN (US)

(73) Assignee: Eli Lilly and Company, Indianaopolis, IN (US)

( * ) Notice: Subject to any disclaimer, the term of this patent is extended or adjusted under 35 U.S.C. 154(b) by 160 days.

(21) Appl. No.: 12/469,724

(22) Filed: May 21, 2009

(65) Prior Publication Data

US 2009/0258820 A1 Oct. 15, 2009

Related U.S. Application Data

(60) Division of application No. 11/216,773, filed on Aug. 30, 2005, now Pat. No. 7,550,428, which is a division of application No. 09/942,458, filed on Aug. 29, 2001, now Pat. No. 7,041,637, which is a continuation of application No. PCT/US00/05508, filed on Mar. 2, 2000.

(60) Provisional application No. 60/122,692, filed on Mar. 3, 1999.

(51) Int. Cl.
*A61K 38/14* (2006.01)
(52) U.S. Cl. .......................................... 514/1.1; 530/317
(58) Field of Classification Search .................. None
See application file for complete search history.

(56) References Cited

U.S. PATENT DOCUMENTS

| | | | |
|---|---|---|---|
| 3,293,482 A | 12/1966 | Wolkstein |
| 3,978,210 A | 8/1976 | Mizuno et al. |
| 4,293,482 A | 10/1981 | Abbott et al. |
| 4,293,483 A | 10/1981 | Debono |
| 4,293,489 A | 10/1981 | Debono |
| 4,299,763 A | 11/1981 | Abbott et al. |
| 4,304,716 A | 12/1981 | Abbott et al. |
| 4,320,052 A | 3/1982 | Abbott et al. |
| 4,348,384 A | 9/1982 | Horikoshi et al. |
| 4,876,241 A | 10/1989 | Feldman et al. |
| 4,927,831 A | 5/1990 | Malamas |
| 5,141,674 A | 8/1992 | Leigh |
| 5,166,135 A | 11/1992 | Schmatz |
| 5,198,421 A | 3/1993 | Chen et al. |
| 5,202,309 A | 4/1993 | Schwartz et al. |
| 5,376,634 A | 12/1994 | Iwamoto et al. |
| 5,541,160 A | 7/1996 | Balkovec et al. |
| 5,573,936 A | 11/1996 | Kreuzman et al. |
| 5,618,787 A | 4/1997 | Jamison et al. |
| 5,629,289 A | 5/1997 | Rodriguez |
| 5,629,290 A | 5/1997 | LaGrandeur et al. |
| 5,646,111 A | 7/1997 | Borromeo et al. |
| 5,652,213 A | 7/1997 | Jamison et al. |
| 5,693,611 A | 12/1997 | Henle et al. |
| 5,696,084 A | 12/1997 | Lartey et al. |
| 5,741,775 A | 4/1998 | Balkovec et al. |
| 5,786,325 A | 7/1998 | Borromeo et al. |
| 5,932,543 A | 8/1999 | Burkhardt et al. |
| 5,952,008 A | 9/1999 | Backstrom et al. |
| 5,965,525 A | 10/1999 | Burkhardt et al. |
| 5,972,996 A | 10/1999 | Nielsen-Kahn et al. |
| 5,985,309 A | 11/1999 | Edwards et al. |
| 5,993,805 A | 11/1999 | Sutton et al. |
| 6,001,336 A | 12/1999 | Gordon |
| 6,043,341 A | 3/2000 | Udodong et al. |
| 6,153,224 A | 11/2000 | Staniforth |
| 6,258,821 B1 | 7/2001 | Stogniew et al. |
| 6,267,958 B1 | 7/2001 | Andya et al. |
| 6,284,277 B1 | 9/2001 | Bouloumie et al. |
| 6,284,282 B1 | 9/2001 | Maa et al. |
| 6,309,623 B1 | 10/2001 | Weers et al. |
| 6,323,176 B1 * | 11/2001 | Jamison et al. .................. 514/3.4 |
| 6,384,013 B1 | 5/2002 | Burkhardt et al. |
| 6,433,040 B1 | 8/2002 | Dellamary et al. |
| 6,451,349 B1 | 9/2002 | Robinson et al. |
| 6,475,523 B1 | 11/2002 | Staniforth |
| 6,506,726 B1 | 1/2003 | Dobbins et al. |
| 6,565,885 B1 | 5/2003 | Tarara et al. |
| 6,590,073 B2 | 7/2003 | Dalder et al. |
| 6,638,495 B2 | 10/2003 | Kabalnov et al. |
| 6,653,281 B1 | 11/2003 | Borromeo et al. |
| 6,660,843 B1 | 12/2003 | Feige et al. |
| 6,670,324 B2 | 12/2003 | Jamison et al. |
| 6,689,390 B2 | 2/2004 | Bernstein et al. |
| 6,709,650 B1 | 3/2004 | Sutton et al. |

(Continued)

FOREIGN PATENT DOCUMENTS

CA 2043762 12/1991

(Continued)

OTHER PUBLICATIONS

Avis, K. E. (1990). "Parenteral Preparations" Chapter 84 *In Remington Pharmaceutical Sciences.* 18$^{th}$ edition, Mack Publishing Company p. 1545-1569.
Longer, M. A. and Robinson, J. R. (1990). "Transdermal Systems" in Chapter 91 *In Remington Pharmaceutical Sciences.* 18$^{th}$ edition, Mack Publishing Company. p. 1690-1693.
Nema, S. et al. (1997). "Excipients and Their Use in Injectable Products," *PDA Journal of Pharm. Science and Tech.* 51(4):166-171.
Sclarra, J. J. and Cutie, A. J. (1990). "Aerosols" Chapter 92 *In Remington Pharmaceutical Sciences.* 18$^{th}$ edition, Mack Publishing Company. p. 1694-1712.
Turco, S. J. (1990). "Intravenous Admixtures." Chapter 85 *In Remington Pharmaceutical Sciences.* 18$^{th}$ edition, Mack Publishing Company. p. 1570-1580.
Ibrahim, F. S. et al., (1995) "The effect of pH, sugars and calcium ion concentration on the thermal stability of whey proteins" *Egyptian J. Dairy Sci.* 23:177-178.

(Continued)

*Primary Examiner* — Christopher R. Tate
*Assistant Examiner* — Roy Teller
(74) *Attorney, Agent, or Firm* — Jennifer A. Kispert; J. Michael Dixon

(57) ABSTRACT

A complex of an echinocandin compound with a carbohydrate is described having improved thermal stability and water solubility. A process for making the echinocandin/carbohydrate complex is also described as well as the use of the complex in pharmaceutical formulations and treatments of fungal infections.

23 Claims, No Drawings

U.S. PATENT DOCUMENTS

| | | | |
|---|---|---|---|
| 6,743,777 B1 | 6/2004 | Burkhardt et al. | |
| 6,916,784 B2 | 7/2005 | Burkhardt et al. | |
| 6,960,564 B2 * | 11/2005 | Milton et al. | 514/3.3 |
| 7,041,637 B2 | 5/2006 | Larew et al. | |
| 2002/0151474 A1 | 10/2002 | Schwier et al. | |
| 2002/0161176 A1 | 10/2002 | Dalder et al. | |
| 2003/0039667 A1 | 2/2003 | Jira et al. | |
| 2003/0054981 A1 | 3/2003 | Milton et al. | |
| 2003/0104048 A1 | 6/2003 | Patel et al. | |
| 2003/0220236 A1 | 11/2003 | Burkhardt et al. | |
| 2004/0223997 A1 | 11/2004 | Stogniew | |

FOREIGN PATENT DOCUMENTS

| | | |
|---|---|---|
| DE | 2803581 A1 | 8/1979 |
| EP | 0031221 A1 | 7/1981 |
| EP | 0032009 A1 | 7/1981 |
| EP | 0359529 A1 | 3/1990 |
| EP | 0359529 B1 | 3/1990 |
| EP | 0365324 A1 | 4/1990 |
| EP | 0365324 B1 | 4/1990 |
| EP | 0447186 A1 | 9/1991 |
| EP | 0448343 A2 | 9/1991 |
| EP | 0448343 A3 | 9/1991 |
| EP | 0448353 A2 | 9/1991 |
| EP | 0448353 A3 | 9/1991 |
| EP | 0448354 A2 | 9/1991 |
| EP | 0448354 A3 | 9/1991 |
| EP | 0448355 A2 | 9/1991 |
| EP | 0448355 A3 | 9/1991 |
| EP | 0448356 A2 | 9/1991 |
| EP | 0448356 A3 | 9/1991 |
| EP | 0460882 A2 | 12/1991 |
| EP | 0460882 A3 | 12/1991 |
| EP | 0460882 B1 | 12/1991 |
| EP | 0462531 A2 | 12/1991 |
| EP | 0462531 B1 | 12/1991 |
| EP | 0486011 A2 | 5/1992 |
| EP | 0486011 A3 | 5/1992 |
| EP | 0503960 A1 | 9/1992 |
| EP | 0525889 A1 | 2/1993 |
| EP | 0561639 A1 | 9/1993 |
| EP | 0561639 B1 | 9/1993 |
| EP | 0589074 | 3/1994 |
| EP | 0744405 | 11/1996 |
| EP | 0757058 | 2/1997 |
| EP | 0931834 | 7/1999 |
| GB | 2241956 A | 9/1991 |
| GB | 2242194 A | 9/1991 |
| JP | 03240727 | 10/1991 |
| JP | 05271097 | 10/1993 |
| JP | 5271097 A | 10/1993 |
| JP | 06172205 | 6/1994 |
| JP | 6172205 A | 6/1994 |
| WO | WO9425048 | 11/1994 |
| WO | WO9527074 A1 | 10/1995 |
| WO | WO9631228 A1 | 10/1996 |
| WO | WO9637509 A1 | 11/1996 |
| WO | WO9637510 A1 | 11/1996 |
| WO | WO9637511 A1 | 11/1996 |
| WO | WO9637512 A1 | 11/1996 |
| WO | WO9705163 A1 | 2/1997 |
| WO | WO9727864 A1 | 8/1997 |
| WO | WO9730695 | 8/1997 |
| WO | WO9906062 | 2/1999 |
| WO | WO9943337 A1 | 9/1999 |
| WO | WO0011023 A2 | 3/2000 |
| WO | WO0011023 A3 | 3/2000 |
| WO | WO0012540 A1 | 3/2000 |
| WO | WO0034315 A2 | 6/2000 |
| WO | WO0034315 A3 | 6/2000 |
| WO | WO0035944 A1 | 6/2000 |
| WO | WO0035945 A1 | 6/2000 |
| WO | WO0051564 A1 | 9/2000 |
| WO | WO0051567 A1 | 9/2000 |
| WO | WO0052036 A1 | 9/2000 |
| WO | WO0052037 A1 | 9/2000 |
| WO | WO03105767 A3 | 12/2003 |

OTHER PUBLICATIONS

Nail, S. L. and Gatlin, L. A. (1993) "Chapter 3: Freeze drying: Principles and practice" *Pharmaceutical Dosage Forms*. Parenteral Medications, vol. 2, $2^{nd}$ Edition, edited by Kenneth, E. A. et al., Marcel Dekker, Inc., pp. 163-233.

Etter, M. C. and Baures, P.W. (1988)"Triphenylphosphine Oxide as a Crystallization Aid," *J. Am. Chem. Soc.* 110:639-640.

Debono, M. et. al. (1995). "Semisynthetic Chemical Modification of the Antifungal Lipopeptide Echinocandin B (ECB): Structure-Activity Studies of the Lipophilic and Geometric Parameters of Polyarylated Acyl Analogs of ECB," *J Med Chem.* 38(17):3271-3281.

Groll, A.H. et al. (2001). "Pharmacokinetic and Pharmacodynamic Modeling of Anidulafungin (LY303366): Reappraisal of Its Efficacy in neutropenic Animal Models of Opportunistic Mycoses Using Optical Plasma Sampling," *Antimicrobial Agents and Chemotherapy* 45(10):2845-2855. International Search Report mailed on Dec. 9, 2003, for PCT Patent Application No. PCT/US03/18754 filed on Jun. 12, 2003, 5 pages.

International Search Report for PCT Application No. PCT/US00/05494 filed Mar. 2, 2000, mailed Jun. 7, 2000, three pages.

International Search Report for PCT Application No. PCT/US00/05508 filed Mar. 2, 2000, mailed Aug. 21, 2000, two pages.

International Search Report for PCT Application No. PCT/US00/05546 filed Mar. 2, 2000, mailed Aug. 11, 2000, three pages.

International Search Report for PCT Application No. PCT/US00/05547 filed Mar. 2, 2000, mailed Jul. 19, 2000, two pages.

Keller-Juslen, C. et al. (1976). "Structure of the Cyclopeptide Antibiotic SL 7810 (=Echinocandin B)." *Tetrahedron Letters* 46:4147-4150.

Turner, W.W. et al. (1996). "Recent Advances in the Medicinal Chemistry of Antifungal Agents." *Current Pharmaceutical Design* 2:209-224.

* cited by examiner

ECHINOCANDIN/CARBOHYDRATE COMPLEXES

CROSS-REFERENCE TO RELATED APPLICATIONS

This application is a divisional of U.S. patent application Ser. No. 11/216,773, filed on Aug. 30, 2005, which is a divisional of U.S. patent application Ser. No. 09/942,458, filed on Aug. 29, 2001, which is a continuation of International Patent Application No. PCT/US00/05508, filed on Mar. 2, 2000, which claims priority to U.S. Provisional Patent Application Ser. No. 60/122,692, filed on Mar. 3, 1999, the contents of which are incorporated herein by reference in their entirety.

FIELD OF THE INVENTION

The present invention relates to pharmaceutically active echinocandin materials, in particular, a crystalline complex between an echinocandin compound and a carbohydrate to enhance stability and water solubility.

BACKGROUND OF THE INVENTION

Echinocandin compounds containing a hemiaminal functionality are generally prone to ring opening at the aminal bond, especially at elevated temperatures. In addition, the amorphous forms of the compounds are sensitive to both humidity and temperatures above −10° C., the amorphous material is not stable above freezer temperatures. This not only effects the shelf-life of the drug in bulk form but also makes it more difficult to handle the compounds in an industrial process.

One approach to eliminate the ring-opening at the aminal bond is to remove or functionalize the hydroxy group of the hemiaminal function; however, this requires an additional synthetic step. Even tough this is a very effective way to increase stability of the modified compound, any additional steps in a manufacturing process reduce productivity, increase potential for waste and increase cost.

U.S. Pat. No. 4,876,241 discloses the use of a sugar as a stabilizer in biological and pharmaceutical products; however, the process is directed to the stabilization of the products during thermal inactivation of viral and bacterial contaminants in solution. The sugar is removed after the thermal inactivation process. Consequently, this process doesn't address the long-term stability of the product.

The stabilization effects of sugars in a thermal process have been shown. For example, the effects of sugars, pH and calcium on the thermal denaturation of whey proteins is discussed in Ibrahim et al. Egyptian J. Dairy Sci., 23:177-188 (1995). Like the previous reference, the stabilizing effects were realized in a liquid form. Neither reference suggests that stability could be enhanced by incorporation of a carbohydrate into the crystalline form of a compound.

In addition to thermal instability, the lipopeptide compounds, such as the echinocandins, are also known to have very poor water solubility (<0.1 mg/ml) which makes them particularly difficult to formulate for parenteral (ip) applications and complicates the purification of the materials. Generally, amorphous materials are more difficult to purity than crystalline materials.

Therefore, there is a need for improved thermal stability and water solubility of echinocandin compounds without effecting bioavailability or making structural changes to the compound as well as providing a means to further purify the echinocandin.

SUMMARY OF THE INVENTION

It has now been found that by crystallizing a echinocandin compound in the presence of a carbohydrate (or simple sugar) gives rise to a crystalline product having improved thermal stability and water solubility without compromising the bioavailability of the active compound. In one embodiment of the present invention, a crystalline complex between an echinocandin compound and a carbohydrate is provided. The complex is characterized in that the echinocandin/carbohydrate complex has a more crystalline form (i.e., more ordered matrix) than the echinocandin compound without the carbohydrate.

In another embodiment of the present invention, a method is provided for making the echinocandin/carbohydrate complex described above comprising the steps of (a) providing an echinocandin compound; (b) mixing the echinocandin compound and a carbohydrate in a solvent to form a mixture; (c) heating the mixture to solubilize the echinocandin compound and to soluble or disperse the carbohydrate; (d) allowing the mixture to cool to produce the echinocandin/carbohydrate complex; and (e) isolating the echinocandin/carbohydrate complex.

In yet another embodiment of the present invention, a process for preparing a parenteral formulation is provided comprising the step of mixing the echinocandin/carbohydrate complex described above in an aqueous solvent.

In another embodiment of the present invention, a pharmaceutical formulation is provided which includes the echinocandin/carbohydrate complex described above and a pharmaceutically acceptable carrier.

In another embodiment of the present invention, a method is provided for treating a fungal infection in a mammal in need thereof, comprising administering to the mammal the echinocandin/carbohydrate complex described above.

In another embodiment, a method is provided for treating an antifungal infection in a mammal in need thereof, which comprises contacting the echinocandin/carbohydrate complex described above with bodily fluids of the mammal, wherein the complex collapses to an amorphous form when contacted with the bodily fluids.

DEFINITIONS

"Complex" refers to an association between the echinocandin compound and carbohydrate so that the complex has a more crystalline form (e.g., more ordered unit matrix) than the corresponding echinocandin compound without the carbohydrate.

"Carbohydrate" refers to an aldehydic or ketonic derivative of polyhydric alcohols represented by the formulas $C_n(H_2O)_n$ (e.g., glucose, $C_6(H_2O)_6$; sucrose, $C_{12}(H_2O)_{11}$). Carbohydrates include compounds with relatively small molecules, such as the simple sugars (e.g., monosaccharides, disaccharides, etc.), as well as macromolecular (polymeric) substances such as starch, glycogen, and cellulose polysaccharides. Sugars are carbohydrates (saccharides) having the general composition $(CH_2O)_n$ and simple derivatives thereof. Although the simple monomeric sugars (glycoses) are described as polyhydroxy aldehydes or ketones, e.g., $HOCH_2$—$(CHOH)_4$—$CHO$ for aldohexoses (e.g., glucose) or $HOCH_2$—$(CHOH)_3$—$CO$—$CH_2OH$ for 2-ketoses (e.g., fructose), the structures are commonly written as five (furanose) or six (pyranose) membered ring cyclic ethers, e.g.

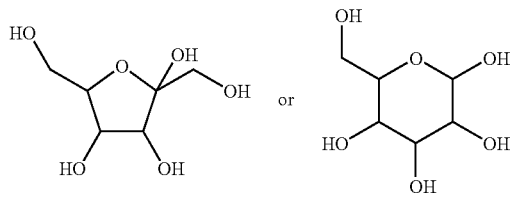

D and L enantiomers, as well as the alpha and beta anomers of the compounds are also included within the definition of carbohydrates.

"Echinocandin" refers to a compound having the following general structure:

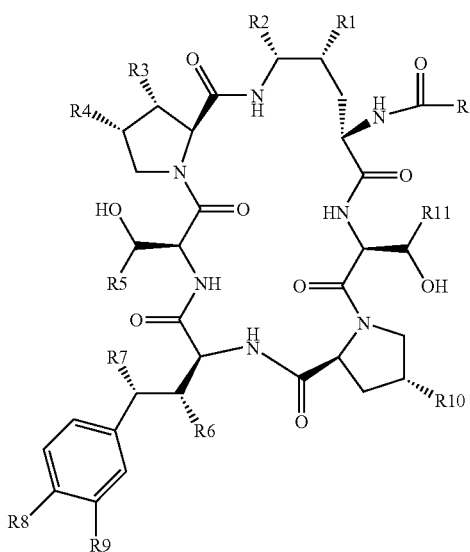

where: R is an alkyl group, an alkenyl group, an alkynyl group, an aryl group, heteroaryl group, or combinations thereof; $R_1$, $R_2$, $R_3$, $R_6$, $R_7$, and $R_{10}$, are independently hydroxy or hydrogen; $R_4$ is hydrogen, methyl or —$CH_2C(O)NH_2$; $R_5$ and $R_{11}$ are independently methyl or hydrogen; $R_8$ is —OH, —$OSO_3H$, —$OPO_3H_2$, —$OPO_3HR^a$, or —$OPO_2HR^a$, where $R^a$ is hydroxy, $C_1$-$C_6$ alkyl, $C_1$-$C_6$ alkoxy, phenyl, phenoxy, p-halophenyl, phalophenoxy, p-nitrophenyl, p-nitrophenoxy, benzyl, benzyloxy, p-halobenzyl, p-halobenzyloxy, p-nitrobenzyl, or p-nitrobenzyloxy; $R_9$ is —H, —OH, or —$OSO_3H$; and pharmaceutically acceptable salts or hydrates thereof.

Even though a specific chiral form is depicted above, other chiral forms are within the spirit of the present invention.

"Echinocandin B" or "ECB" refers to a echinocandin compound as described above where $R_1$, $R_2$, $R_3$, $R_6$, $R_7$, $R_8$ and $R_{10}$ are hydroxy groups; $R_4$, $R_5$ and $R_{11}$ are methyl groups; $R_9$ is a hydrogen. In the natural product, R is a linoleoyl group. In a particularly useful semi-synthetic compound, R has both a rigid and a flexible component, for example where R is represented by the following formula

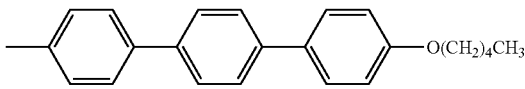

"Alkyl" refers to a hydrocarbon radical of the general formula CnH2n+1 containing from 1 to 30 carbon atoms unless otherwise indicated. The alkane radical may be straight, branched, cyclic, or multi-cyclic. The alkane radical may be substituted or unsubstituted. Similarly, the alkyl portion of an alkoxy group or alkanoate have the same definition as above.

"Alkenyl" refers to an acyclic hydrocarbon containing at least one carbon-carbon double bond. The alkene radical may be straight, branched, cyclic, or multi-cyclic. The alkene radical may be substituted or unsubstituted.

"Alkynyl" refers to an acyclic hydrocarbon containing at least one carbon carbon triple bond. The alkyne radical may be straight, or branched. The alkyne radical may be substituted or unsubstituted.

"Aryl" refers to aromatic moieties having single (e.g., phenyl) or fused ring systems (e.g., naphthalene, anthracene, phenanthrene, etc.). The aryl groups may be substituted or unsubstituted. Substituted aryl groups include a chain of aromatic moieties (e.g., biphenyl, terphenyl, phenylnaphthalyl, etc.).

"Heteroaryl" refers to aromatic moieties containing at least one heteroatom within the aromatic ring system (e.g., pyrrole, pyridine, indole, thiophene, furan, benzofuran, imidazole, pyrimidine, purine, benzimidazole, quinoline, etc.). The aromatic moiety may consist of a single or fused ring system. The heteroaryl groups may be substituted or unsubstituted.

Within the field of organic chemistry and particularly within the field of organic biochemistry, it is widely understood that significant substitution of compounds is tolerated or even useful. In the present invention, for example, the term alkyl group allows for substituents which is a classic alkyl, such as methyl, ethyl, isopropyl, isobutyl, tertiary butyl, hexyl, isooctyl, dodecyl, stearyl, etc. The term specifically envisions and allows for substitutions on alkyls which are common in the art, such as hydroxy, halogen, alkoxy, carbonyl, keto, ester, carbamato, etc., as well as including the unsubstituted alkyl moiety. However, it is generally understood by those skilled in the art that the substituents should be selected so as to not adversely affect the pharmacological characteristics of the compound or adversely interfere with the use of the medicament. Suitable substituents for any of the groups defined above include alkyl, alkenyl, alkynyl, aryl, halo, hydroxy, alkoxy, aryloxy, mercapto, alkylthio, arylthio, mono- and di-alkyl amino, quaternary ammonium salts, aminoalkoxy, hydroxyalkylamino, aminoalkylthio, carbamyl, carbonyl, carboxy, glycolyl, glycyl, hydrazino, guanyl, and combinations thereof.

DETAILED DESCRIPTION

Attempts to crystallize Echinocandin B from a solvent such as methanol provided crystalline product containing the solvent in sufficient purity; however, this material degraded as the solvent evaporated. Applicants have discovered that when the crystallization process is performed in the presence of a carbohydrate (or sugar), a crystalline complex is formed between the echinocandin compound and the carbohydrate. Although not wishing to be bound by any particular theory, it is believed that the carbohydrate becomes incorporated into the open spaces within the crystalline unit cell of the echinocandin. As a result, the carbohydrate acts like a non-volatile solvate. An analogous complex was reported by Etter and co-workers using triphenyl phosphine oxide (*J. Am. Chem. Soc.*, 110:639-640 (1988)). An advantage of an inclusion complex is the extraction of the carbohydrate (or sugar) from the matrix thus causing the remaining crystalline structure to collapse to an amorphous solid. Amorphous solids are generally regarded to be more bioavailable. As a result, the echinocandin/carbohydrate complex may revert to an amorphous form in vivo (e.g., when contacted with bodily fluids of the mammal being treated) thus optimizing the bioavailability during treatment.

It is believed that the aminal group is stabilized by means of hydrogen bonding between the carbohydrate and the aminal functionality. This theory is supported by the observation that the carbohydrate is released immediately upon dispersion of the crystalline complex in water.

The complexes are formed using standard crystallization procedures such as those typically performed for purifying compounds by recrystallization. The echinocandin material and carbohydrate are dissolved at an elevated temperature (approximately 40 to 60° C., preferably less than 55° C.) in a solvent. The solution is then slowly cooled until the crystallization begins. A seed crystal (such as a previously crystallized complex or an insoluble sugar) may be added to initiate crystallization. Suitable solvents include any solvent, or mixture of solvents, inert to the ongoing reaction that sufficiently solubilizes the reactants to afford a medium within which to effect the desired complexation between the carbohydrate and the echinocandin compound, such as protic or ketone solvents including methanol, ethanol, benzyl alcohol, as well as mixtures of benzyl alcohol with solvents such as methanol, ethanol, n-propanol, isopropanol, n-butanol, 2-butanol, 1-butanol, 2-pentanol, 2-methyl-1-propanol, MEK, acetone, ethyl acetate, toluene, acetonitrile, fluorobenzene, methylene chloride, nitromethane, or cyclic ketones such as cyclopentanone and cyclohexanone. Preferred solvents include methanol, ethanol, benzyl alcohol, and mixtures of benzyl alcohol with methyl ethyl ketone, ethyl acetate, and acetonitrile.

Suitable carbohydrates include adonitol, arabinose, arabitol, ascorbic acid, chitin, D-cellobiose, 2-deoxy-D-ribose, dulcitol, (S)-(+)-erythrulose, fructose, fucose, galactose, glucose, inositol, lactose, lactulose, lyxose, maltitol, maltose, maltotriose, mannitol, mannose, melezitose, melibiose, microcrystalline cellulose, palatinose, pentaerythritol, raffinose, rhamnose, ribose, sorbitol, sorbose, starch, sucrose, trehalose, xylitol, xylose and hydrates thereof. Suitable carbohydrates also include the D and L enantiomers, as well as the alpha and beta anomers of the compounds listed above. Preferred carbohydrates are the simple sugars (e.g., mono- and di-saccharides). For better understanding, the sugars (or carbohydrates) may be grouped into four classifications: insoluble, soluble, highly soluble and co-crystallizing. For illustrative purposes only, the following definitions were used for the four classifications when methanol was used as the recrystallizing solvent for the semi-synthetic echinocandin compound 6(a) depicted in the Examples below.

The insoluble carbohydrates are defined as those having low or no solubility in methanol (<3 equivalents) at 40-60° C. The insoluble carbohydrates impart little or no enhancement to the order as determined by X-ray powder diffraction (XRPD). Even though the complexes formed were heterogeneous, the complexes demonstrated improved thermal stability in comparison to the amorphous echinocandin product. Examples of insoluble carbohydrates in methanol include D-arabinose, L-arabinose, D-cellubiose, dulcitol, L-fucose, D-galactose, α-D-glucose, β-D-glucose, L-glucose, inisitol, α-D-lactose hydrate, lactulose, L-lyxose, maltitol, D-maltose hydrate, maltotriose hydrate, mannitol, melezitose hydrate, α-D-melibiose hydrate, microcrystalline cellulose, palatinose hydrate, L-sorbose, starch, and sucrose.

Soluble carbohydrates are defined as those carbohydrates that are soluble in, methanol from 2 to 20 equivalents at 40-60° C. A homogeneous product is formed with the echinocandin compound under a set of specific equivalent ranges. Carbohydrates that fall within this class demonstrate both enhanced order by XRPD and enhanced stability in comparison to the amorphous echinocandin product alone. Soluble carbohydrate compositions not only exhibit improved thermal stability in comparison to the amorphous compound but have also demonstrated improved dispersement properties in water. Examples of carbohydrates in this class for methanol as a solvent include adonitol, L-arabinose, D-arabitol, L-arabitol, 2-deoxy-D-ribose, (S)-(+)-erythrulose hydrate, d-fructose, D-(+)-fucose, L-fucose, α-D-glucose, β-D-glucose, L-glucose, D-lyxose, L-lyxose, D-maltose hydrate, D-mannose, L-mannose, melezitose hydrate, palatinose hydrate, pentaerthritol, L-rhamnose, D-ribose, L-ribulose hydrate, D-sorbitol, sucrose, D-trehalose, xylitol and D-xylose.

Highly soluble carbohydrates are those having extremely high solubility in a solution containing methanol and the echinocandin compound (>20 equivalents) at 40-60° C. These exhibit enhanced order in the isolated complex as determined by XRPD but do not contain any heterogeneous carbohydrate. The complex also exhibits enhanced thermal stability in comparison to the amorphous echinocandin product Examples of highly soluble carbohydrates include 2-deoxy-D-ribose, (S)-(+)-erythrulose hydrate, L-fucose, L-rhamnose, D-ribose and L-ribulose hydrate.

Co-crystallizing carbohydrates are defined as those carbohydrates having good solubility in methanol (>2 equivalents) at 40-60° C. Upon cooling the homogeneous mixture of the echinocandin compound and the carbohydrate demonstrates enhanced order by XRPD and enhanced stability in comparison to the amorphous echinocandin. Examples of co-crystallizing carbohydrates in methanol include adonitol, D-arabitol, L-arabitol, D-raffinose pentahydrate, D-sorbitol, D-trehalose hydrate, xylitol and L-xylose. The co-crystalline compositions not only exhibit improved thermal stability in comparison to the amorphous compound but have also demonstrated improved dispersement properties in water. Thus the co-crystalline complexes have the potential of assisting or improving in vivo dispersion of the bulk drug.

Each of the carbohydrates generally fall within more than one class with the exception of some insoluble carbohydrates. For example, adonitol is very soluble in methanol; however, addition of higher equivalents of adonitol remain soluble in the test solution but co-crystallize upon cooling. Therefore, adonitol is classified as both a soluble and a co-crystallizing carbohydrate in methanol.

For illustrative purposes, the semi-synthetic echinocandin Compound 6(a) (semi-ECB) was recrystallized in the presence of each of the carbohydrates listed in Table 1 to form the corresponding semi-ECB/carbohydrate complex in methanol. Each of the complexes were then tested for thermal stability using the following general procedure.

Thermal Stability Stress Test

Prior to placing the sample on a two week stress stability test, each sample was re-assayed for potency and total related substances (TRS) to obtain a true T0 point. The samples (including a control of amorphous ECB) were placed in sealed vials at 50° C. for 2 weeks and then assayed for potency and TRS at the end of the test. The major degradation impurity was used to track overall stability. Degradation rate was determined as the relative ratio of the main degradation product, Peak B of the test material vs. the control, Recovery is termed "Rec." A decrease in degradation rate implies a greater thermal stability of the comparative test materials. Table 1 summarizes the results in comparison to the control sample.

Potency (Pot) and TRS were determined using a high-pressure, liquid chromatograph (HPLC) equipped with a 15 cm×4.6 mm, 3.5 micron particle size, Zorbax™ XDB-C18 colorful The samples were eluted with a 0.85% w/w aqueous phosphoric acid solution and a 95% aqueous acetonitrile solution using methanol as the diluent. A gradient elution scheme was used where the ratio of the phosphoric acid solution to the acetonitrile solution was varied from 95:5 to 59:41 to 5:95 to 95:5 over an hour period. In Table 1, *Values before stress testing Recorded in weight percent instead of weight equivalents* KF=Karl Fischer % water (coulombic).

TABLE 1

| ECB/Sugar Complex | Wt Equiv Sugar | Deg. Rate | Pot (%) | TRS (%) | KF*** (%) | Rec (%) |
|---|---|---|---|---|---|---|
| Control | 0 | 1.0 | 92.8* | 3.83* | 3.12* | NA |
|  |  |  | 85.7 | 9.03 | NA | NA |
| Adonitol | 4.0 | 0.5 | 92.7 | 1.77 | 3.40 | 73.3 |
|  | 8.0 | 0.5 | 57.9 | 1.56 | 2.30 | 75.6 |
| D-Arabinose | 3.0 | 0.5 | 78.6 | 2.92 | 2.32 | 75.0 |
| L-Arabinose | 3.0 | 0.3 | 88.1 | 1.44 | 4.54 | 77.8 |
|  | 4.3 | 0.4 | 71.0 | 2.53 | 2.49 | 82.4 |
| D-Arabitol | 8.0 | 0.4 | 85.9 | 1.64 | 3.22 | 68.5 |
|  | 22.6 | 0.3 | 20.0 | 2.85 | 0.76 | 72.9 |
| L-Arabitol | 8.0 | 0.3 | 88.9 | 1.57 | 2.40 | 79.6 |
|  | 21.2 | 0.4 | 25.3 | 2.88 | 1.00 | 79.9 |
| Dcellubiose | 0.5 | 0.8 | 77.4 | 3.20 | 1.47 | 74.9 |
| Poly(N-acetyl D-glucosamine | 28.0** | 0.6 | 68.7 | 4.63 | NA | 81.1 |
| 2-Deoxy-D-ribose | 8.0 | 0.4 | 91.6 | 1.34 | 3.91 | 65.7 |
|  | 33.6 | 0.2 | 68.0 | 2.35 | NA | 54.8 |
| Dulcitol | 1.4 | 0.5 | 73.8 | 3.42 | 1.49 | 77.6 |
| (S)-(+)-Erythrulose | 8.0 | 0.2 | 92.6 | 1.67 | 2.72 | 68.1 |
|  | 30.0 | 0.7 | 78.0 | 2.50 | 1.50 | 71.0 |
| D-Fructose | 8.0 | 0.3 | 85.6 | 2.31 | 3.71 | 83.4 |
|  | 20.0 | 0.4 | 84.1 | 2.21 | 1.73 | 67.3 |
|  | 30.0 | 0.4 | 24.8 | 0.67 | 0.56 | 70.5 |
| D-(+)-Fucose | 4.0 | 0.3 | 91.9 | 1.46 | 3.15 | 77.8 |
|  | 16.0 | 0.3 | 61.7 | 2.48 | 1.83 | 67.7 |
| L-Fucose | 1.0 | 0.6 | 93.5 | 1.71 | 4.07 | 55.6 |
|  | 33.5 | 0.1 | 13.9 | 2.20 | NA | 17.1 |
| D-Galactose | 1.4 | 0.6 | 80.6 | 3.28 | 1.53 | 74.3 |
| α-D-Glucose | 3.3 | 0.4 | 87.5 | 1.79 | 3.47 | 66.0 |
|  | 4.0 | 0.4 | 54.8 | 2.99 | 1.63 | 66.1 |
| β-D-Glucose | 4.0 | 0.4 | 86.4 | 1.61 | 3.38 | 81.1 |
|  | 4.7 | 0.3 | 67.9 | 2.60 | 2.17 | 77.5 |
| L-Glucose | 4.0 | 0.4 | 86.8 | 1.81 | 4.70 | 70.8 |
|  | 8.4 | 0.4 | 49.7 | 2.64 | 0.79 | 77.6 |
| Inositol | 1.1 | 0.6 | 77.2 | 3.49 | 1.72 | 77.2 |
| α-D-Lactose | 1.1 | 0.5 | 69.4 | 3.57 | 1.54 | 81.9 |
| Lactulose | 2.5 | 0.6 | 57.1 | 3.83 | 1.75 | 76.6 |
| D-Lyxose | 8.0 | 0.3 | 92.9 | 1.49 | 3.21 | 66.1 |
|  | 16.0 | 0.4 | 89.8 | 2.26 | 2.20 | 57.3 |
| L-Lyxose | 10.4 | 0.4 | 86.7 | 2.56 | 1.77 | 76.7 |
|  | 13.9 | 0.3 | 89.5 | 2.15 | 1.99 | 76.2 |
| Maltitol | 1.5 | 0.4 | 63.1 | 1.87 | 0.72 | 82.3 |
| D-Maltose | 8.0 | 0.3 | 82.0 | 1.44 | 2.86 | 56.8 |
|  | 8.5 | 0.2 | 67.3 | 1.66 | 1.75 | 59.5 |
| Maltotriose | 4.0 | 0.2 | 74.6 | 1.67 | 2.57 | 68.2 |
|  | 9.3 | 0.1 | 49.7 | 1.73 | 2.07 | 61.9 |
| Mannitol | 1.8 | 0.5 | 65.2 | 3.67 | NA | 75.8 |
| D-Mannose | 4.0 | 0.5 | 90.3 | 2.30 | 2.27 | 87.4 |
|  | 12.0 | 0.4 | 53.7 | 2.40 | 1.69 | 83.8 |
| L-Mannose | 4.0 | 0.5 | 88.7 | 2.71 | 1.05 | 77.8% |
| Melezitose | 1.0 | 0.3 | 78.6 | 1.75 | 3.60 | 86.3% |
|  | 1.9 | 0.3 | 58.4 | 2.45 | 2.22 | 94.9 |
| α-D-Melibiose | 1.3 | 0.6 | 65.9 | 2.16 | 0.65 | 77.9 |

TABLE 1-continued

| ECB/Sugar Complex | Wt Equiv Sugar | Deg. Rate | Pot (%) | TRS (%) | KF*** (%) | Rec (%) |
|---|---|---|---|---|---|---|
| Micro-crystalline Cellulose | 14%** | 0.9 | 79.3 | 3.24 | 1.09 | 80.3 |
| Palatinose | 2.0 | 0.2 | 78.1 | 1.62 | 2.76 | 71.4 |
|  | 8.6 | 0.3 | 62.0 | 2.27 | 2.50 | 73.3 |
| Pentaerythritol | 4.0 | 0.5 | 70.8 | 3.64 | NA | 80.8 |
| D-Raffinose | 1.0 | 0.3 | 85.1 | 1.77 | 4.31 | 72.0 |
|  | 4.0 | 0.5 | 45.6 | 1.73 | 3.99 | 75.8 |
| L-Rhamnose | 2.0 | 0.4 | 93.2 | 1.46 | 4.88 | 60.0 |
|  | 20.0 | 0.5 | 92.4 | 2.19 | 2.34 | 51.8 |
| D-Ribose | 13.0 | 0.4 | 89.1 | 1.09 | NA | 77.0 |
|  | 25.0 | 0.5 | 88.1 | 1.25 | NA | 72.6 |
| D-Sorbitol | 6.4 | 0.4 | 55.0 | 3.30 | 3.59 | 93.4 |
|  | 7.2 | 0.2 | 57.4 | 1.48 | NA | 87.3 |
| L-Sorbose | 4.5 | 0.5 | 59.7 | 2.10 | 0.78 | 80.6 |
| Starch | 14%** | 0.8 | 78.8 | 3.24 | 1.63 | 77.2 |
| Sucrose | 1.0 | 0.5 | 86.8 | 2.94 | NA | 69.4 |
|  | 2.1 | 0.7 | 57.5 | 2.07 | 0.59 | 83.2 |
| D-Trehalose | 0.4 | 0.3 | 93.0 | 1.48 | NA | 88.4 |
|  | 1.3 | 0.3 | 68.8 | 1.47 | NA | 89.0 |
| Xylitol | 5.5 | 0.3 | 91.6 | 1.33 | NA | 78.6 |
|  | 11.0 | 0.3 | 55.4 | 1.29 | NA | 80.8 |
| D-Xylose | 2.6 | 0.6 | 91.1 | 3.05 | 5.20 | 83.6 |
| L-Xylose | 3.0 | 0.3 | 66.5 | 1.62 | 2.27 | 64.4 |

Each of the carbohydrates tested showed an improvement in thermal stability in comparison to the control where no carbohydrate was added. Even though the insoluble carbohydrates did not perform as well as the other classes, an improvement over the amorphous form of the ECB was observed none-the-less. The data also shows that the thermal stability can be optimized by using the appropriate weight equivalents of sugar added. For example, (S)-(+)-erythrulose provided a more stable complex when only 8.0 weight equivalents are added instead of 30.0 weight equivalents to the methanol crystallization process. Whereas, 2-deoxy-D-ribose provides a more stable complex when 33.6 weight equivalents of the sugar is used instead of 8.0 weight equivalents. For an echinocandin/fructose complex, preferably the complex contains between about 7 and 14% w/w fructose, more preferably between about 8.5 and 11% w/w fructose. In general, the weight percent of carbohydrate in the echinocandin/carbohydrate complex is between 5 and 35% depending upon the carbohydrate used.

The carbohydrate crystallization process has been observed to reduce the level of typical degradation impurities on the order of about 80 to 90%. Fermentation impurities were generally reduced about 5 to 20%. Overall, total related substances (TRS) were reduced by about 45-55%. For comparison, the crystallization process for fructose is approximately 6% more efficient at impurity rejection than straight methanol recrystallization for Compound 6(a).

Preferred carbohydrate complexes with semi-ECB crystallized from methanol include carbohydrates selected from L-arabinose, D-arabitol, L-arabitol, 2-deoxy-D-ribose, (S)-(+)-erythrulose, D-fructose, D-(+)-fucose, L-fucose, D-galactose, α-D-glucose, β-D-glucose, L-glucose, D-lyxose, L-lyxose, maltitol, D-maltose, maltotriose, D-mannose, melezitose, palatinose, D-raffinose, L-rhamnose, D-ribose, D-sorbitol, D-trehalose, xylitol, L-xylose and hydrates thereof. More preferred are semi-ECB/carbohydrate complexes where the carbohydrate is selected from L-arabinose, D-arabitol, L-arabitol, 2-deoxy-D-ribose, (S)-(+)-erythrulose, D-fructose, D-(+)-fucose, L-fucose, D-galactose, β-D-glucose, D-lyxose, L-lyxose, D-maltose, maltotriose, melezitose, palatinose, D-raffinose, D-sorbitol, D-trehalose, xylitol, L-xylose and hydrates thereof.

The cyclic peptides used in the present invention may be produced by culturing various microorganisms. Suitable natural product starting materials belonging to the echinocandin cyclic peptide family include Echinocandin B, Echinocandin C, Echinocandin D, Aculeacin Aγ, Mulundocandin, Sporiofungin A, Pneumocandin $A_0$, WF1899A, and Pneumocandin $B_0$. In general, the cyclic peptides may be characterized as a cyclic hexapeptide nucleus with an acylated amino group on one of the amino acids. The amino group on the naturally-occurring cyclic peptide is typically acylated with a fatty acid group forming a side chain off the nucleus. Examples of naturally-occurring acyl groups include linoleoyl (Echinocandin B, C and D), palmitoyl (Aculeacin Aγ and WF11899A), stearoyl, 12-methylmyristoyl (Mulundocandin), 10,12-dimethylmyristoyl (Sporiofungin A and Pneumocandin $A_0$) and the like.

Semi-synthetic derivatives may be prepared by removing the fatty acid side chain from the cyclic peptide nucleus to produce a free amino group (i.e., no pendant acyl group —C(O)R). The free amine is then reacylated with a suitable acyl group. For example, the echinocandin B nucleus has been re-acylated with certain non-naturally occurring side chain moieties to provide a number of antifungal agents. See, i.e., U.S. Pat. No. 4,293,489 (Debono). Those skilled in the art will appreciate that the N-acyl side chain encompasses a variety of side chain moieties known in the art. Suitable side chain moieties include substituted and unsubstituted alkyl groups, alkenyl groups, alkynyl groups, aryl groups, heteroaryl groups and combinations thereof. Preferably, the side chain contains both a linearly rigid section and a flexible alkyl section to maximize antifungal potency. Representative examples of preferred acyl side chains include R groups having the following structures:

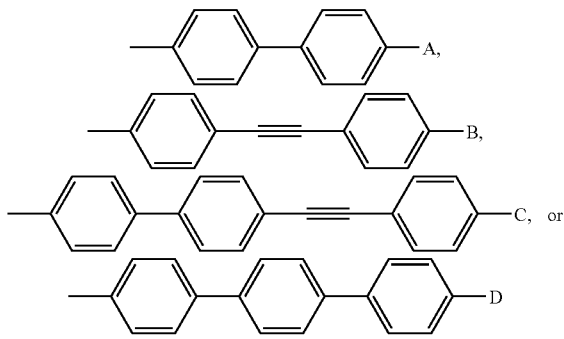

where A, B, C and D are independently hydrogen, $C_1$-$C_{12}$ alkyl, $C_2$-$C_{12}$ alkynyl, $C_1$-$C_{12}$ alkoxy, $C_1$-$C_{12}$ alkylthio, halo, —O—$(CH_2)_m$—[O—$CH_2)_n]_p$—O—($C_1$-$C_{12}$ alkyl) or —O—$(CH_2)_q$—X-E; m is 2, 3 or 4; n is 2, 3 or 4; p is 0 or 1; q is 2, 3 or 4; X is pyrrolidino, piperidino or piperazino; and E is hydrogen, $C_1$-$C_{12}$ alkyl, $C_3$-$C_{12}$ cycloalkyl, bell or $C_3$-$C_{12}$ cycloalkylmethyl.

As noted above, the cyclic peptides described herein may be prepared by fermentation of known microorganisms as described in the art. The subsequent deacylation is typically carded out enzymatically using a deacylase enzyme by known materials and procedures described in the art.

For example, U.S. Pat. No. 3,293,482 describes the deacylation and preparation of the cyclic peptide of formula I where $R_4$, $R_5$, and $R_{11}$ are methyl, $R_9$ is hydrogen, and $R_1$, $R_2$, $R_3$, $R_6$, $R_7$, $R_8$ and $R_{10}$ are each hydroxy. U.S. Pat. No. 4,299,763 describes the deacylation and preparation of the cyclic peptide of formula I where $R_4$, $R_5$, and $R_{11}$ are methyl, $R_2$ is hydroxy, $R_7$ and $R_9$ are hydrogen and $R_1$, $R_3$, $R_6$, $R_8$ and $R_{10}$ are each hydroxy. U.S. Pat. No. 3,978,210 describes the preparation of aculeacin. U.S. Pat. No. 4,304,716, describes the deacylation and preparation of the cyclic peptide of formula I where $R_5$ is —$CH_2C(O)NH_2$; $R_{11}$ is methyl; $R_4$ and $R_9$ are hydrogen; $R_1$, $R_2$, $R_3$, $R_6$, $R_7$, $R_8$ and $R_{10}$ are each hydroxy and the acyl group with substituent R is myristoyl.

Cyclic peptides where $R_2$ and $R_7$ are each hydrogen may be prepared by subjecting the corresponding compound (where $R_2$ and $R_7$ are each hydroxy; the ornithine alpha-amino group may be a free amino group or acylated) to a strong acid and a reducing agent at a temperature of between −5° C. and 70° C., in a suitable solvent. Suitable strong acids include trichloroacetic acid, trifluoroacetic acid or boron trifluoride etherate. A preferred strong acid is trifluoroacetic acid. Suitable reducing agents include sodium cyanoborohydride or triethylsilane. A preferred reducing agent is triethylsilane. Suitable solvents include methylene chloride, chloroform or acetic acid, preferably methylene chloride. The strong acid is present in an amount from about 2 to 60 mol per mol of substrate, and the reducing agent is present in an amount from about 2 to 60 mol per mol of substrate. The acid reduction process selectively removes the aminal ($R_2$) and benzylic ($R_7$) hydroxy groups.

Acylation of the α-amino group on the ornithine unit may be accomplished in a variety of ways well known in the art. For example, the amino group may be acylated by reaction with an appropriately substituted acyl halide, preferably in the presence of an acid scavenger such as a tertiary amine (e.g., triethylamine). The reaction is typically carried out at a temperature between about −20° C. to 25° C. Suitable reaction solvents include polar aprotic solvents, such as dioxane or dimethylformamide. Solvent choice is not critical so long as the solvent employed is inert to the ongoing reaction and the reactants are sufficiently solubilized to effect the desired reaction.

The amino group may also be acylated by reaction with an appropriately substituted carboxylic acid, in the presence of a coupling agent. Suitable coupling agents include dicyclohexylcarbodiimide (DCC), N,N'-carbonyldiimidazole, bis(2-oxo-3-oxazolidinyl)phosphinic chloride (BOP-Cl), N-ethoxycarbonyl-2-ethoxy-1,2-dihydroquinoline (EEDQ), benzotriazole-1-yloxy-tripyrrolidinophosphonium hexafluorophosphate (PyBOP) and the like.

Alternately, the amino group may be acylated with an activated ester of a carboxylic acid such as p-nitrophenyl, 2,4,5-trichlorophenyl, hydroxybenzotriazole hydrate (HOBT.$H_2O$), pentafluorophenol, and N-hydroxysuccinimide carboxylate esters. Preferred acylating moieties are the 2,4,5-trichlorophenyl and HOBT carboxylate esters. The reaction is typically ran 1 to 65 hours at a temperature from about 0° C. to 30° C. in an aprotic solvent. The reaction is generally complete after about 24 to 48 hours when carried out at a temperature between about 15° C. to 30° C. Suitable solvents include tetrahydrofuran and dimethylformamide or mixtures thereof. The amino group is generally present in equimolar proportions relative to the activated ester or with a slight excess of the amino group.

The R—COOH precursor acids are prepared by hydrolyzing a nitrile of the formula R—CN or an ester of the formula R—COO($C_1$-$C_4$ alkyl). The nitrile and ester intermediates may be prepared using procedures known in the art. For example, the nitrile and ester intermediates where R is an alkoxy aryl moiety may be prepared using Procedure A or Procedure B.

Procedure A One equivalent of an alkyl bromide, iodide, or p-toluenesulfonate is added to a mixture containing one equivalent of a base, such as potassium t-butoxide or potassium carbonate ($K_2CO_3$), and one equivalent of an hydroxy aryl compound in 200-300 ml of acetonitrile ($CH_3CN$). The reaction mixture is refluxed for 6 h and then concentrated in vacuo to provide a residue which is dissolved in a $Et_2O$/2N NaOH mixture. The resulting layers are separated and the organic layer is dried over magnesium sulfate ($MgSO_4$), filtered and dried to provide the alkoxy aryl product.

Procedure B Diethylazodicarboxylate (1 equiv.) is added dropwise to a mixture containing an hydroxy aryl compound (1 equiv.), an alkyl alcohol (1 equiv.) and triphenylphosphine (1 equiv.) in 200-300 ml of THF. After 17 h, the solvent is removed in vacuo to provide a residue which is dissolved in $Et_2O$. The resulting mixture is washed with a 2N NaOH solution, dried over $MgSO_4$, filtered and concentrated to provide a product which is then crystallized from a $Et_2O$/pentane mixture or, if the product contains a tertiary amine, the hydrochloride salt is formed and crystallized from a methanol (MeOH)/EtOAc mixture. The nitrile and ester intermediates where R is an alkynyl aryl moiety may be prepared using Procedure C.

Procedure C A mixture containing $Et_2O$ (2 equiv.), palladium dichloride (0.05 equiv.), triphenylphosphine (0.1 equiv.), cuprous iodide (0.025 equiv.) and an alkyne (1 equiv.) is added to one equivalent of an aryl bromide, iodide, or trifluoromethanesulfonate in $CH_3CN$ (600 ml/0.1 mol of aryl reactant), under nitrogen ($N_2$). The resulting mixture is refluxed for 17 h and then the solvent is removed in vacuo to provide a residue which is slurred in 300 ml of $Et_2O$ and then filtered. The filtrate is washed with a 1N HCl solution, dried over $MgSO_4$, filtered and then dried to provide the product. The ester intermediates where R is a terphenyl moiety may be prepared using Procedure D.

Procedure D

1. Formation of Boronic Acid Reactant

Butyl lithium (1.2 equivalents) is added to one equivalent of a cold (−78° C.) aryl halide in THF. After 15 minutes, triisopropyl borate (2 equiv.) is added. After 10 minutes, the reaction mixture is warmed to room temperature and quenched by the addition of water ($H_2O$), followed by the addition of 1N HCl. The resulting layers are separated and the organic layer is concentrated in vacuo to provide a solid which is collected by filtration and washed with hexane.

2. Formation of Terphenyl Ester

Tetrakis(triphenylphosphine)palladium (0.03 equiv.) is added to a mixture containing an aryl boronic acid (1 equiv.), $K_2CO_3$ (1.5 equiv.) and methyl 4-iodobenzoate (1 equiv.) (or trichlorophenyl ester of iodobenzoate) in $N_2$-purged toluene. The reaction mixture is refluxed for 7 h and then decanted to remove the $K_2CO_3$ and dried in vacuo to provide a residue. This residue is triturated in $CH_3CN$ and filtered to provide the product. The aryl nitrites and esters described above may be converted to the corresponding carboxylic acids by hydrolysis using Procedure E or Procedure F.

Procedure E An aryl nitrile is dissolved in ethanol (EtOH) and an excess of 50% NaOH solution and refluxed for 2 h. Water is added to the reaction mixture until a solid precipitates. This solid is collected by filtration, added to a dioxane/6N HCl mixture and the resulting mixture is refluxed for 17 h. When the reaction is substantially complete, the carboxylic acid product is crystallized by the addition of H2O and then collected by filtration and dried in vacuo.

Procedure F An excess of 2N NaOH is added to an aryl ester in MeOH, and the resulting solution is refluxed for 5 h and then acidified by the addition of excess HCl. Water is added to the reaction mixture until a solid (carboxylic acid) precipitates. The carboxylic acid is collected by filtration and dried in vacuo.

The carboxylic acids may be converted to the corresponding 2,4,5-trichlorophenyl esters using Procedure G. The activated esters are then used to acylate the amino nucleus.

Procedure G A mixture containing an aryl carboxylic acid (1 equiv.), 2,4,5-trichlorophenol (1 equiv.) and DCC (1 equiv.) in $CH_2C_{12}$ is stirred for 17 h and then filtered. The filtrate is concentrated to provide a residue which is dissolved in $Et_2O$, filtered, and then pentane is added until crystallization begins. The crystals are collected by filtration and dried in vacuo. Alternatively, the carboxylic acid may be activated by conversion to the corresponding hydroxybenzotriazole ester using Procedure H.

Procedure H An aryl carboxylic acid (1 equiv.) and a slight excess of N-mesylate substituted hydroxybenzotriazole (1.2 equiv.) were reacted in the presence of a slight excess of a base such as triethylamine ($Et_3N$) (1.3 equiv.) in DMF, under $N_2$. When the reaction was complete, the mixture was diluted with toluene and washed with $H_2O$. The organic portion was diluted with $H_2O$ and then filtered using t-butyl methyl ether (MTBE) for transferring the material. The resultant solid was washed with MTBE and then dried in vacuo.

The echinocandin compound may be isolated and used per se or in the form of its pharmaceutically acceptable salt or hydrate in the preparation of the carbohydrate complex. The carbohydrate complex with the echinocandin compound is prepared as described earlier. "Pharmaceutically acceptable salt" refers to non-toxic acid addition salts derived from inorganic and organic acids. Suitable salt derivatives include halides, thiocyanates, sulfates, bisulfates, sulfites, bisulfites, arylsulfonates, alkylsulfates, phosphonates, monohydrogenphosphates, dihydrogenphosphates, metaphosphates, pyrophosphonates, alkanoates, cycloalkylalkanoates, arylalkonates, adipates, alginates, aspartates, benzoates, fumarates, glucoheptanoates, glycerophosphates, lactates, maleates, nicotinates, oxalates, palmitates, pectinates, picrates, pivalates, succinates, tartarates, citrates, camphorates, camphorsulfonates, digluconates, trifluoroacetates, and the like.

A typical solution formulation is prepared by mixing the echinocandin carbohydrate complex and a surfactant (preferably a micelle-forming surfactant) in a solvent. The formulation may optionally include one or more of a buffer, a stabilizing agent, and/or a tonicity agent. Solvents are generally selected based on those recognized as safe (GRAS) to be administered parenterally to a mammal. In general, safe solvents are non-toxic aqueous solvents such as, water and other nontoxic solvents that are soluble or miscible in water. Suitable aqueous solvents include water, ethanol, propylene glycol, polyethylene glycols (e.g., PEG400, PEG300), etc. and mixtures thereof. A preferred solvent is water.

A typical freeze-dried formulation includes the echinocandin/carbohydrate complex, a surfactant (preferably a micelle-forming surfactant), a bulking agent and/or a stabilizing agent. The addition of a micelle-forming surfactant not only optimizes the reconstitution of the freeze-dried formulation in an aqueous solvent but also provides enhanced stability to the freeze-dried materials. The formulation may optionally include one or more buffering agents. Some examples of suitable parenteral solution and freeze-dried formulations including their preparations may be found in U.S. patent application Ser. No. 60/122,623.

Both solution and freeze-dried formulations may optionally contain a stabilizing agent. A stabilizing agent is generally present at a concentration in the range from about 0.5% to about 40% (wgt./vol.), more preferably at a concentration in the range from about 1% to about 6%. "Stabilizing agent" refers to a pharmaceutically acceptable excipient that enhances the chemical and physical stability of the active ingredient in the formulation. Suitable stabilizing agents include polyols (e.g., polyethylene and propylene glycols and carbohydrates such as sucrose, trehalose, fructose, lactose and mannitol), amino acids and surfactants such as polysorbates and bile salts. Preferred stabilizing agents for freeze dried formulation include mannitol, sucrose, trehalose, fructose, lactose and combinations thereof. In solution most preferred stabilizing agents are the bile salts, polyethylene glycols and propylene glycol.

Both solution and freeze-dried formulations may also optionally contain a buffer. The buffer is present at a concentration in the range from about 0.03% to about 5% (wgt./vol.), more preferably at a concentration in the range from about 0.1% to about 1%. "Buffer" refers to a pharmaceutically acceptable excipient that maintains the pH of the solution within a particular range specific to the buffering system. A suitable pH range is from pH 3.0 to 7.0. The preferred range is from 4.0 to 5.5, more preferably 4.0 to 5.0. Suitable buffers include acetates, citrates, phosphates, tartrates, lactates, succinates, amino acids and the like. Preferred buffers for the solution formulation include acetate, citrate, tartrates, phosphate salts and combinations thereof. In the freeze dried formulation, the preferred buffer is tartaric acid.

Solution formulation may optionally contain one or more tonicity agents. The tonicity agent is generally present at a concentration in the range from about 1 to about 100 mg/ml, more preferably in the range from about 9 to about 50 mg/ml. "Tonicity agent" refers to a pharmaceutically acceptable excipient that makes a solution compatible with blood. Tonicity agents are particularly desirable in injectable formulations. Suitable tonicity agents include glycerin, lactose, mannitol, dextrose, sodium chloride, sodium sulfate, sorbitol and the like. Preferred tonicity agents include mannitol, sorbitol, lactose, sodium chloride and combinations thereof.

When freeze-dried, the formulations may optionally contain a bulking agent. The bulking agent is present in a formulation at a concentration in the range from about 2% to about 10% (wgt./vol.), more preferably at a concentration in the range from about 3% to about 6%. "Bulking agent" refers to a pharmaceutically acceptable excipient that adds bulk to a formulation which results in a well-formed cake upon freeze drying. Suitable bulking agents include mannitol, glycine, lactose, sucrose, trehalose, dextran, hydroxyethyl starch, ficoll and gelatin. Preferred bulking agents include mannitol, sucrose, trehalose, lactose and combinations thereof.

The formulations may be prepared using conventional dissolution and mixing procedures. For example, the bulk drug substance (e.g., echinocandin carbohydrate complex) is dissolved in a suitable solvent in the presence of a surfactant and optionally one or more bulking agents, buffers, stabilizing agents and/or tonicity agents. The resulting solution is sterile filtered and preferably freeze-dried to provide the desired formulation. Prior to freeze-drying, the surfactant is generally present in an amount greater than 1% weight per volume of solution. A suitable method for freeze-drying is described in Nail et al. Freeze Drying Principles and Practice, in Pharmaceutical Dosage Forms, 2nd Ed., Marcel Dekker, Inc. NY, pp. 163-233 (1993).

In general, freeze-dried formulations contain a bulking agent and non freeze-dried formulations contain one or more tonicity agents. In application, the formulations are typically diluted or reconstituted (if freeze-dried) and further diluted if necessary, prior to administration. An example of reconstitution instructions for the freeze-dried product are to add ten ml of water for injection (WFI) to the vial and gently agitate to dissolve. Typical reconstitution times are less than one minute. The resulting solution is then further diluted in an infusion solution such as dextrose 5% in water (D5W), prior to administration.

The active ingredient is typically formulated into pharmaceutical dosage forms to provide an easily controllable dosage of the drug and to give the patient an elegant and easily handleable product. Formulations may comprise from 0.1% to 99.9% by weight of active ingredient, more generally from about 10% to about 30% by weight.

As used herein, "unit dose" or "unit dosage" refers to physically discrete units that contain a predetermined quantity of active ingredient calculated to produce a desired therapeutic effect. When a unit dose is administered orally or parenterally, it is typically provided in the form of a tablet, capsule, pill, powder packet, topical composition, suppository, wafer, measured units in ampoules or in multidose containers, etc. Alternatively, a unit dose may be administered in the form of a dry or liquid aerosol which may be inhaled or sprayed.

The dosage to be administered may vary depending upon the physical characteristics of the patient, the severity of the patient's symptoms, and the means used to administer the drug. The specific dose for a given patient is usually set by the judgment of the attending physician.

Suitable carriers, diluents and excipients are well known in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the active ingredient is being applied. The formulations may also include wetting agents, lubricating agents, emulsifiers, suspending agents, preservatives, sweeteners, perfuming agents, flavoring agents and combinations thereof.

A pharmaceutical composition may be administered using a variety of methods. Suitable methods include topical (e.g., ointments or sprays), oral, injection and inhalation. The particular treatment method used will depend upon the type of infection being addressed.

Echinocandin-type compounds have been shown to exhibit antifungal and antiparasitic activity such as growth inhibition of various infectious fungi including *Candida* spp. (i.e., *C. Albicans, C. Parapsilosis, C. Krusei, C. Glabrata, C. Tropicalis,* or *C. Lusitaniaw*); *Torulopus* spp. (i.e., *T. Glabrala*); *Aspergillus* spp. (i.e., *A. Fumigatus*); *Histoplasma* spp. (i.e., *H. Capsulatum*); *Cryptococcus* spp. (i.e., *C. Neoformans*); *Blastomyces* spp. (i.e., *B. Dermatitidis*); *Fusariurm* spp.; *Trichophyton* spp., *Pseutallescheria boydii, Coccidioides immits, Sporothrix schenckii,* etc.

Compounds of this type also inhibit the growth of certain organisms primarily responsible for opportunistic infections in immunosuppressed individuals, such as growth inhibition of *Pneumocystis carinii* (the causative organism of pneumocystis pneumonia (PCP) in AIDS and other immunocompromised patients. Other protozoans that are inhibited by echinocandin-type compounds include *Plasmodium* spp., *Leishmania* spp., *Trypanosoma* spp., *Cryptosporidium* spp., *Isospora* spp., *Cyclospora* spp., *Trichomnas* spp., *Microsporidiosis* spp., etc.

Consequently, the formulations of the present invention are useful in combating either systemic fungal infections or fungal skin infections. Accordingly, the echinocandin/carbohydrate complex (including the formulations and processes used therein) may be used in the manufacture of a medicament for the therapeutic applications described herein. For example, fungal activity (preferably, *Candida albicans* or *Aspergillus fumigatis* activity) or parasitic activity may be inhibited by contacting the echinocandin/carbohydrate complex of the present invention with a fungus or parasite, respectively. "Contacting" includes a union or junction, or apparent touching or mutual tangency of a compound of the invention with a parasite or fungus. The term does not imply any further limitations to the process, such as by mechanism of inhibition. The methods are defined to encompass the inhibition of parasitic and fungal activity by the action of the compounds and their inherent antiparasitic and antifungal properties.

A method for treating a fungal infection which comprises administering an effective amount of a pharmaceutical formulation of the present invention to a host in need of such treatment is also provided. A preferred method includes treating a *Candida albicans* or *Aspergillus fumigatis* infection. "Effective amount" refers to an amount of active compound which is capable of inhibiting fungal activity. The dose administered will vary depending on such factors as the nature and severity of the infection, the age and general health of the host and the tolerance of the host to the antifungal agent. The particular dose regimen likewise may vary according to these factors. The medicament may be given in a single daily dose or in multiple doses during the day. The regimen may last from about 2-3 days to about 2-3 weeks or longer. A typical daily dose (administered in single or divided doses) contains a dosage level between about 0.01 mg/kg to 100 mg/kg of body weight of an active compound. Preferred daily doses are generally between about 0.1 mg/kg to 60 mg/kg and more preferably between about 2.5 mg/kg to 40 mg/kg.

The following examples are provided to illustrate but not limit the invention. All references cited herein are hereby incorporated herein by reference.

EXAMPLES

The echinocandin compound used to exemplify the formulations of the present invention was prepared as described in the following preparations. Specifically, the following sequence describes the preparation of a carbohydrate (fructose) complex with an echinocandin compound 6(a) having the following structure:

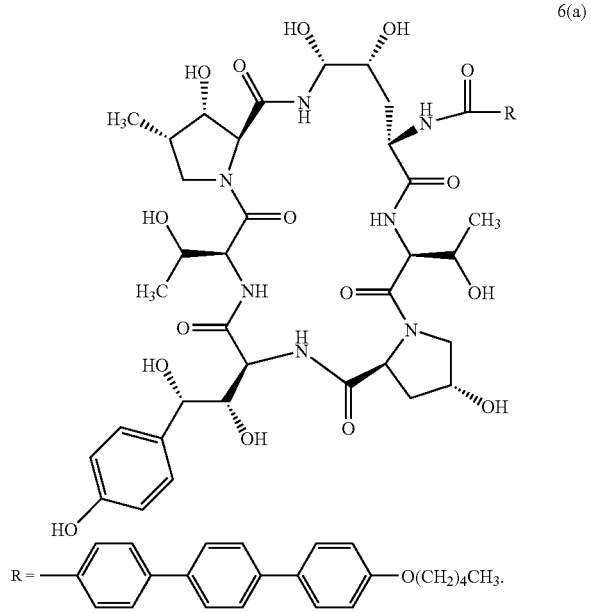

It will be understood by those skilled in the art that the following serves as an illustrative example and that other semi-synthetic echinocandin compounds useful as anti-fungal agents may be synthesized using similar procedures or procedures described in references cited earlier in the specification. Materials used in the following preparations are available from Aldrich Chemicals (Milwaukee, Wis.) unless designated otherwise.

Compound Preparations

Preparation of 4-Bromo-4'-pentyloxybiphenyl 1(a)

Anhydrous $K_2CO_3$ (416$_g$, 3 mol) was added to a mixture of 4-bromo-4'-hydroxybiphenyl (300 g, 1.2 mol), 1-iodopentane (234 ml, 1.79 mol) and 2-butanone (600 ml). The reaction mixture was refluxed for 44 h until TLC (85:15 hexanes/EtOAc) showed complete consumption of the bromo alcohol. The mixture was cooled to about 30° C., diluted with $CH_2C_{12}$ (600 ml) and then filtered. The filtrate was washed twice with $H_2O$ and twice with a saturated aqueous NaCl solution, dried over anhydrous $Na_2SO_4$, filtered and then dried at reduced pressure to provide a solid. This solid was isolated by filtration, washed repeatedly with a total of 2 L of ice-cold heptane to remove all traces of iodopentane and then dried overnight under high vacuum. Yield: 340 g (88%) of a white powder.

Alternative Preparation of 4-bromo-4'-pentyloxybiphenyl 1(a)

4-Bromo-4'-hydroxybiphenyl (12.5 g, 50.2 mmol) was added to a solution of NaOH (2.28 g, 97% pure, 55.2 mmol) in deionized $H_2O$ (150 ml), followed by the addition of 1-iodopentane (11.9 g, 60.2 mmol) and tetrabutylammonium bromide (0.82 g, 2.51 mmol). The mixture was stirred at 90° C. for 3.75 h until the solids went into solution. Then, as the reaction proceeded, the desired product began to precipitate. The mixture was slowly cooled and then filtered to provide a solid which was washed with deionized water until the pH of the filtrate was neutral and then dried for 16 h in a vacuum oven at 30° C. Yield: 15.41 g (96%) of 5a. $R_f$ 0.5 (97:3 hexanes/EtOAc). 1H NMR: δ 0.93 (t, 3H, J=6.9 Hz); 1.41 (m, 4H); 1.79 (m, 2H); 3.97 (t, 2H, J=6.6 Hz); 6.98 (m, 2H); 7-23 (m, 6H). $^{13}C$ NMR: δ 14.03; 22.43; 28.22; 28.98; 68.12; 114.91; 120.71; 127.93; 128.27; 131.77; 132.24; 139.82; 159.03. MS(FAB$^+$): m/z 320. IR(CHC$_{13}$): 2960, 2936, 2874, 1608, 1518, 1485, 1475 cm$^{-1}$. Analysis for $C_{17}H_{19}BrO$: Calcd: C, 63.96; H, 6.00; Br, 25.0. Found: C, 64.10; H, 5.97; Br, 25.28.

Preparation of 4-Boronic acid-4'-pentyloxybiphenyl 2(a)

To a cold (−20° C.) mixture of Compound 1(a) (100 g, 0.31 mol) in t-butylmethylether (MTBE) (1 L), was slowly added n-butyl lithium (150 ml of a 2.5M hexanes solution, 0.37 mol) dropwise under $N_2$, while maintaining the internal temperature between −19° and −18° C. The resultant mixture was stirred for 3.5 h between −17° and −16° C. which resulted in light yellow-green solution. This solution was cooled to −78° C. and diluted with 100 ml of anhydrous THF which resulted in a white precipitate. Then, a cold (−78° C.) solution of triisopropylborate (145 ml, 0.62 mol) in MTBE (200 ml), under nitrogen was added dropwise over 1.5 h while maintaining the reaction temperature between −78° and −74° C. The resultant reaction mixture was stirred for 1.5 h at −78° C., then allowed to warm to −50° C. over 1 h at which time the cooling bath was removed and the mixture was stirred overnight (16-21 h) which resulted in a white precipitate. The mixture was shaken vigorously with 2M HCl (1000 ml) for 5 minutes and then the resulting layers were separated and the organic layer was dried at reduced pressure to provide a residue. This residue was diluted with MTBE (100 ml), followed by heptane (800 ml) to provide a white powder which isolated by suction filtration and washed 3 times with heptane (300 ml). Yield: 88 g (98%). $R_f$ 0.45 (95:5 $CH_2Cl_2$/MeOH). $^1$H NMR: δ 0.92 (m, 3H); 1.41 (m, 4H); 1.80 (m, 2H); 4.00 (m, 2H); 6.99 (m, 2H); 7.45-7.63 (m, 3H); 7.67 (m, 2H); 8.24 (d, 1H, J=8.3 Hz). $^{13}$C NMR: 14.01; 22.26; 28.03; 28.77; 39.61; 39.89; 40.17; 40.45; 67.82; 114.77; 125.32; 127.83; 132.93; 134.84; 141.88; 158.71. MS(FD$^+$): m/z 284. IR(CHCl$_3$): 2959, 2952, 2874, 1606, 1526, 1500 cm$_{-1}$.

Preparation of Compound 3(a)

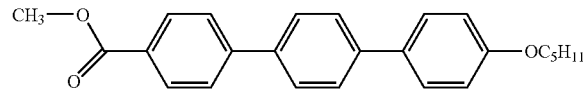

3(a)

A solution of toluene (174 ml) and propanol (20 ml) was degassed 3 times by applying vacuum to the solution for 20-30 seconds followed by purging with $N_2$. A 2M solution of $Na_2CO_3$ was also degassed. The toluene/propanol solution (97 ml) was added to a mixture of methyl 4-iodobenzoate (14.12 g, 53.9 mmol) and Compound 2a) (15.0 g, 52.8 mmol), followed by a degassed 2M aqueous $Na_2CO_3$ solution (29 ml, 58 mmol). The resultant mixture was degassed 2 times for 20-30 seconds each under a positive pressure of $N_2$, followed by the addition of palladium (II) acetate (0.24 g, 1.1 mmol) and triphenylphosphine (0.84 g, 3.2 mmol) and then degassed 2 more times. The reaction mixture was then refluxed under $N_2$ for 5 h resulting in a light-yellow mixture. This mixture was cooled to 23° C. resulting in the formation of a precipitate which was collected by filtration, washed successively with toluene (123 ml), 2:1 MTBE/EtOAc (143 ml), deionized water (123 ml) and 2:1 MTBE/EtOAc (42 ml) and then dried for 16 h in a vacuum oven at 35° C. Yield: 18.7 g (94%). $R_f$ 0.48 (benzene). $^1$NMR: δ 0.93 (t 3H, J=6.80 Hz); 1.42 (m, 4H); 1.81 (m, 2H); 3.95 (s, 3H); 4.00 (t 21, J=6.48 Hz); 6.97 (d, 21, J=8.52 Hz); 7.55 (d, 2H, J=8.52 Hz); 7.66 (m, 6H); 8.10 (d, 2H, J=8.20 Hz). MS(FD$^+$): m/z 374. IR(KBr): 2938, 1723 cm$^{-1}$. Analysis for $C_{25}H_{26}O_3$: Calcd: C, 80.18; H, 7.00. Found: C, 79.91; H, 6.94.

Preparation of Compound 4(a)

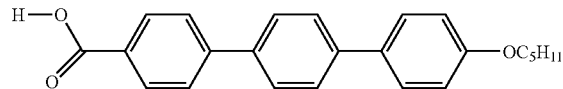

4(a)

A mixture of Compound 3(a) (80 g, 0.21 mol), 5M KOH (160 ml) and cetyltrimethylammonium bromide (4.8 g, 0.013 mol) in xylene (800 ml) was refluxed for 3 h and then cooled to 10° C. and filtered to provide a white solid. This solid was washed 3 times with $H_2O$ (500 ml each) to remove the catalyst and most of the base. The resultant material was treated with DME (500 ml). The pH of the solution was adjusted to pH by the addition of 6M HCl (100 ml). The resultant mixture was refluxed for 30 minutes while periodically checking the pH to assure that it remained acidic, then cooled and filtered. The resulting solid was washed successively with MTBE (400 ml) and water (4×400 ml) until the washings were neutral to litmus. Yield: 76 g (98% yield). $^1$H NMR δ 0.89 (t, 3H, J=6.82 Hz), 1.38 (m, 4H), 1.73 (m, 2H), 3.96 (t, 2H, J=6.3 Hz), 6.95 (d, 2H, J=8.56 Hz), 7.57 (d, 2H, J=8.54 Hz), 7.64-7.74 (m, 6H), 8.00 (d, 2H, J=8.21 Hz), 8.09 (s, 1H). MS(FD$^+$) m/z 360. IR(KBr): 2958, 2937, 2872, 1688 cm$^{-1}$. Analysis for $C_{24}H_{24}O_3$: Calcd: C, 79.97; H, 6.71. Found: C, 80.50; H, 6.77.

Preparation of HOBT Ester of Compound 4(a)

A. Formation of HOBT Mesylate

To a cold (0° C.) mixture of hydroxybenzotriazole hydrate (200 g, 1.48 mol) in anhydrous $CH_2Cl_2$ (1.5 L), was slowly added anhydrous $Et_3N$ (268 ml, 1.92 mol) while maintaining a temperature of 0-10° C., followed by the addition of methanesulfonyl chloride (126 ml, 1.63 mol) while maintaining a temperature of 0-5° C. The resultant mixture was stirred for 3 h at 0° C. and washed successively with cold water (2×1.2 L) and brine (1.2 L). The combined organic extracts were concentrated at reduced pressure to provide a solid. This solid was recrystallized from $CH_2C_{12}$ (100 ml) and heptane (1 L). The crystals were collected by suction filtration and washed repeatedly with a total of 1 L of heptane and then dried overnight under high vacuum (0.5 mm Hg). Yield: 245 g (78%) $R_f$ 0.55 (1:1 hexanes/$CH_2C_{12}$). $^1$H NMR. δ 3.58 (s, 3H), 7.46 (t, 1H, J=7.60 Hz), 7.60 (d, 1H, J=8.28 Hz), 7.65 (d, 1H, J=8.56 Hz), 7.68 (d, 1H, J=8.20 Hz), 8.05 (d, 1H, J=8.41 Hz).

B. Formation of HOBT Ester

A mixture of Compound 4a (50 g, 0.14 mol) and the material described above in part A (36 g, 0.17 mol) in DMF (650 ml) was treated dropwise with $Et_3N$ (25 ml, 0.18 mol), under $N_2$. The resultant mixture was stirred for 4 h at room temperature until all the acid was consumed, as determined by TLC (95:5 $CH_2Cl_2$/MeOH). When all the acid was consumed, an aliquot of the reaction mixture (~3 pipes drops) gave a clear homogeneous solution when diluted with 3 ml of 1:1 $CH_2C_2$/THF. The reaction mixture was then diluted with toluene (500 ml), washed with water (500 ml). The organic layer (containing solid product) was diluted with water (500 ml) and filtered using MTBE for transferring. The solid was rinsed with MTBE (2×400 ml) and dried under vacuum to provide green-white flakes of material. NOTE: This material could be dissolved in THF and filtered to remove any remaining metal contamination. Yield: 61 g (92%). $R_f$ 0.68 (1:1 $CH_2Cl_2$/hexanes). $^1$H NMR: δ 0.93 (t, 3H, J=7.0 Hz), 1.42 (m, 4H), 1.81 (m, 2H), 4.00 (t, 2H, J=6.53 Hz), 6.99 (d, 2H, J=8.6 Hz), 7.42-7.59 (m, 5H), 7.71 (dd, 4H, J=13.91 Hz, 8.40 Hz), 7.86 (d, 2H, J=8.30 Hz), 8.11 (d, 1H, J=8.31 Hz), 8.35 (d, 2H, J=8.33 Hz). $^{13}$C NMR: δ 14.03, 22.44, 28.18, 28.94, 40.10, 40.37, 68.11, 108.45, 110.11, 114.95, 118.71, 120.48, 123.04, 124.94, 124.99, 127.00, 127.23, 127.51, 127.73, 128.06, 128.82, 128.86, 131.35, 132.30, 137.15, 141.43, 143.54, 147.85, 159.15, 162.73. MS(FD$^+$): m/z 477. IR(CHCl$_3$): 2960, 2936, 2874, 1783, 1606 cm$^{-1}$. Analysis for $C_{30}H_{27}N_3O_3$: Calcd: C, 75.45; H, 5.70; N, 8.80. Found: C, 75.69; H, 5.58; N, 8.92.

Preparation of Anti-Fungal Compound 6(a)

Deionized water was used throughout the procedure. A mixture of Compound 5 (11 g, 23 mmol) and the nucleus of Compound 6a) (where R is hydrogen—92% pure by HPLC, 19.25 g, 22.2 mmol) in anhydrous DMF (275 ml) was stirred, under $N_2$ for 4 h (until HPLC showed complete consumption of the cyclic peptide starting material). The mixture was filtered through a bed of celite and the filtrate was concentrated under reduced pressure at 35° C. to provide a paste that could be stirred. This paste was poured into MTBE (500 ml) which resulted in the precipitation of a fine powder which was collected by vacuum filtration and dried to provide 27 g of crude material. This material was crushed to a powder with a mortar and pestle, slurried for 5 minutes in toluene (200 ml), suction filtered (slow filtered), rinsed with MTBE (100 ml) and then dried in vacuo to provide a yellow solid. Yield: 23 g (95% pure by HPLC, retention time=7.79 min).

Alternatively, the conversion may be carried out using an excess of the cyclic nucleus (1.1 equiv.). When the reaction is substantially complete, as indicated by HPLC, the crude material (10 g of a powder) is added portion-wise to a vigorously stirred mixture of 9:1 acetone/water (60 ml). Celite (2.5 g, pre-washed with a 9:1 acetone/water mixture) is added to the resultant suspension. After stirring for 2 minutes, the mixture is filtered through a bed of celite (prewashed with 9:1 acetone/water) and the cake is rinsed twice with 9:1 acetone/water (10 ml). The filtrate is poured into a beaker of deionized water (200 ml) while gently swirling the mixture which resulted in the formation of a precipitate. This precipitate is collected by suction filtration, rinsed with $H_2O$ (4×25 ml), and then dried in vacuo at room temperature. Yield: 6.81 g (97% pure by HPLC).

The product was fitter purified using preparatory HPLC chromatography. $R_f$ 0.29 (80:20 $CHCl_3$/MeOH). MS(FAB$^+$): m/z for $C_{58}H_{74}N_7O_7$, Calcd: 1140.5141. Found: 1140.5103. IR(KBr): 3365, 2934, 1632, 1518 cm$^{-1}$.

Preparation of Fructose Complex with Compound 6(a)

A jacketed reactor was charged with 1 equivalent of Compound 6(a), 8 equivalents of fructose and a sufficient quantity of methanol to make 58 mg/ml of Compound 6(a). The mixture was heated to 50-55° C. until the dissolution was complete, The solution was cooled to 45° C. After seeding at 45° C., the seeded solution was cooled to 25° C. at a cooling rate of −2 degrees/hour. The mixture was further cooled to 0° C. over 2 hours (cooling rate=−12.5 degrees/hour) and then stirred at 0° C. for 12 hours. The product was isolated by vacuum filtration, washed with cold methanol containing 1% fructose on a weight/weight basis, and then dried 24 hours in a 30° C. vacuum oven.

Assays were performed on a gradient HPLC system equipped with a 15 cm×4.6 mm, 3.5 micron particle size Zorbax™ SB-C18 or XDB-C18 analytical column.

We claim:
1. An echinocandin/carbohydrate complex prepared by the steps of:
   (a) providing an echinocandin compound represented by the following structure

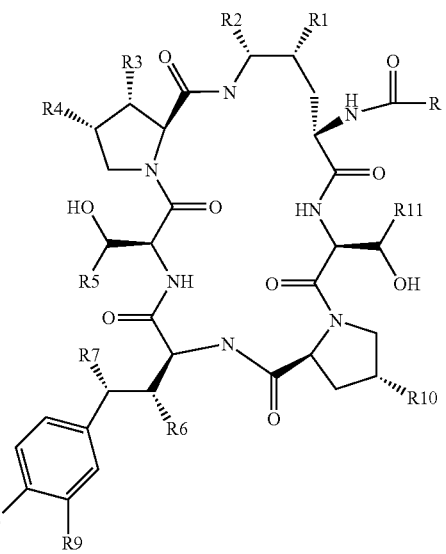

wherein
   R is an alkyl group, an alkenyl group, an alkynyl group, an aryl group, heteroaryl group, or combinations thereof,
   $R_1$, $R_2$, $R_3$, $R_6$, $R_7$ and $R_{10}$ are independently hydroxy or hydrogen,
   $R_4$ is hydrogen, methyl or —$CH_2C(O)NH_2$,
   $R_5$ and $R_{11}$ are independently methyl or hydrogen,
   $R_8$ is —OH, —$OSO_3H$, —$OPO_3H_2$, —$OPO_3HR^a$, or —$OPO_2HR^a$, where $R^a$ is hydroxy, $C_1$-$C_6$ alkyl, $C_1$-$C_6$ alkoxy, phenyl, phenoxy, p-halophenyl, p-halophenoxy, p-nitrophenyl, p-nitrophenoxy, benzyl, benzyloxy, p-halobenzyl, p-halobenzyloxy, p-nitrobenzyl, or p-nitrobenzyloxy;
   $R_9$ is —H, —OH, or —$OSO_3H$, and pharmaceutically acceptable salts or hydrates thereof;
   (b) mixing together said echinocandin compound of step (a) to a carbohydrate in a solvent to form a mixture;
   (c) heating said mixture to solubilize said echinocandin compound and to solubilize or disperse said carbohydrate;
   (d) allowing said mixture to cool to produce said echinocandin/carbohydrate complex; and
   (e) isolating said echinocandin/carbohydrate complex.
2. The complex of claim 1 wherein
   $R_4$, $R_5$ and $R_{11}$ are each methyl;
   $R_2$ and $R_7$ are independently hydrogen or hydroxyl; $R_1$, $R_3$, $R_6$ and $R_{10}$ are each hydroxy;
   $R_8$ is —OH, —$OPO_3HR^a$, or —$OPO_2HR^a$, where $R^a$ is methyl;
   R is linoleoyl, palmitoyl, stearoyl, myristoyl, 12-methylmyristoyl, 10,12-dimethylmyristoyl, or a group having the general structure:

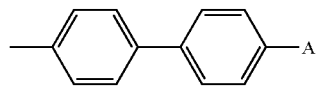

-continued

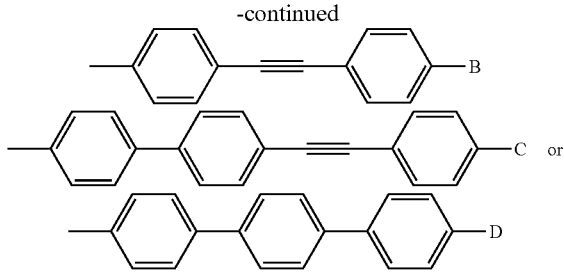

where A, B, C, and D are independently hydrogen, $C_1$-$C_{12}$ alkyl, $C_2$-$C_{12}$ alkynyl, $C_1$-$C_{12}$ alkoxy, $C_1$-$C_{12}$ alkylthio, halo, or —O—$(CH_2)_m$—[O—$(CH_2)$n]p-O—($C_1$-$C_{12}$ alkyl) or —O—$(CH_2)_q$—X-E;

m is 2, 3 or 4;
n is 2, 3 or 4; p is 0 or 1; q is 2, 3 or 4;
X is pyrrolidino, piperidino or piperazino;
E is hydrogen, $C_1$-$C_{12}$ alkyl, $C_3$-$C_{12}$ cycloalkyl, benzyl or $C_3$-$C_{12}$ cycloalkylmethyl.

3. The complex of claim 2 wherein
$R_2$ and $R_7$ are each hydroxyl;
$R_8$ is hydroxy; and

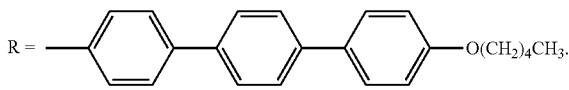

4. The complex of claim 1 wherein said carbohydrate is selected from the group consisting of adonitol, arabinose, arabitol, ascorbic acid, chitin, D-cellubiose, 2-deoxy-D-ribose, dulcitol, (S)-(+)-erythrulose, fructose, fucose, galactose, glucose, inositol, lactose, lactulose, lyxose, maltitol, maltose, maltotriose, mannitol, mannose, melezitose, melibiose, microcrystalline cellulose, palatinose, pentaerythritol, raffinose, rhamnose, ribose, sorbitol, sorbose, starch, sucrose, trehalose, xylitol, xylose and hydrates thereof.

5. The complex of claim 3 wherein said carbohydrate is selected from the group consisting of L-arabinose, D-arabitol, L-arabitol, 2-deoxy-D-ribose, (S)-(+)-erythrulose, D-fructose, D-(+)-fucose, L-fucose, D-galactose, α-D-glucose, glucose, L-glucose, D-lyxose, L-lyxose, maltitol, D-maltose, maltotriose, D-mannose, melezitose, palatinose, D-raffinose, L-rhamnose, D-ribose, D-sorbitol, D-trehalose, xylitol, L-xylose and hydrates thereof.

6. The complex of claim 3 wherein said carbohydrate is selected from the group consisting of L-arabinose, D-arabitol, L-arabitol, 2-deoxy-D-ribose, (S)-(+)-erythrulose, D-fructose, D-(+)-fucose, L-fucose, D-galactose, β-D-glucose, D-lyxose, L-lyxose, D-maltose, maltotriose, melezitose, palatinose, D-raffinose, D-sorbitol, D-trehalose, xylitol, L-xylose and hydrates thereof.

7. The complex of claim 1 wherein said solvent is selected from the group consisting of methanol, ethanol, benzyl alcohol, mixtures of benzyl alcohol with methanol, ethanol, n-propanol, isopropanol, n-butanol, 2-butanol, i-butanol, 2-pentanol, 2-methyl-1-propanol, MEK, acetone, ethyl acetate, toluene, acetonitrile, fluorobenezene, methylene chloride, nitromethane, cyclopentanone and cyclohexanone.

8. The complex of claim 7 wherein said solvent is selected from the group consisting of methanol, ethanol, benzyl alcohol, and mixtures of benzyl alcohol with methyl ethyl ketone, ethyl acetate, and acetonitrile.

9. The complex of claim 8 wherein said solvent is methanol.

10. The complex of claim 9 wherein said carbohydrate is soluble in said methanol when heated to about 40° to 60° C.

11. The complex of claim 9 wherein said carbohydrate is highly soluble in said methanol when heated to about 40° to 60° C.

12. The complex of claim 9 wherein said carbohydrate is insoluble in said methanol when heated to about 40° to 60° C.

13. The complex of claim 1 wherein said carbohydrate co-crystallizes with said echinocandin compound.

14. A method for treating a fungal infection in a mammal in need thereof, which comprises administering to said mammal the echinocandin/carbohydrate complex of claim 1.

15. The method of claim 14 wherein said fungal infection arises from *Candida albicans* or *Aspergillus fumigatis* activity.

16. A method for treating a fungal infection in a mammal in need thereof, which comprises contacting a echinocandin/carbohydrate complex of claim 1 with bodily fluids of said mammal, wherein said complex collapses to an amorphous form when contact with said bodily fluids.

17. The method of claim 16 wherein said fungal infection arises from *Candida albicans* or *Aspergillus fumigatis* activity.

18. A method for treating a fungal infection in a mammal in need thereof, which comprises administering to said mammal the echinocandin/carbohydrate complex of claim 2.

19. A method for treating a fungal infection in a mammal in need thereof, which comprises administering to said mammal the echinocandin/carbohydrate complex of claim 3.

20. A method for treating a fungal infection in a mammal in need thereof, which comprises administering to said mammal the echinocandin/carbohydrate complex of claim 4.

21. A method for treating a fungal infection in a mammal in need thereof, which comprises contacting the echinocandin/carbohydrate complex of claim 2 with bodily fluids of said mammal, wherein said complex collapses to an amorphous form when contacted with said bodily fluids.

22. A method for treating a fungal infection in a mammal in need thereof, which comprises contacting the echinocandin/carbohydrate complex of claim 3 with bodily fluids of said mammal, wherein said complex collapses to an amorphous form when contacted with said bodily fluids.

23. A method for treating a fungal infection in a mammal in need thereof, which comprises contacting the echinocandin/carbohydrate complex of claim 4 with bodily fluids of said mammal, wherein said complex collapses to an amorphous form when contacted with said bodily fluids.

\* \* \* \* \*